(12) United States Patent
Portney

(10) Patent No.: US 7,097,660 B2
(45) Date of Patent: Aug. 29, 2006

(54) ACCOMMODATING INTRAOCULAR LENS

(76) Inventor: Valdemar Portney, 11940 N. Riviera, Tustin, CA (US) 92782

( * ) Notice: Subject to any disclaimer, the term of this patent is extended or adjusted under 35 U.S.C. 154(b) by 372 days.

(21) Appl. No.: 10/016,705

(22) Filed: Dec. 10, 2001

(65) Prior Publication Data
US 2003/0109926 A1 Jun. 12, 2003

(51) Int. Cl.
*A61F 2/16* (2006.01)
(52) U.S. Cl. .............. 623/6.22; 623/6.37; 623/6.34
(58) Field of Classification Search ........... 623/6.18, 623/6.32–6.37, 6.39–6.4
See application file for complete search history.

(56) References Cited

U.S. PATENT DOCUMENTS

| | | | |
|---|---|---|---|
| 4,409,691 A | 10/1983 | Levy | |
| 4,790,847 A | 12/1988 | Woods | |
| 4,816,030 A | * 3/1989 | Robinson | 623/6.51 |
| 4,816,031 A | 3/1989 | Pfoff | |
| 4,842,601 A | 6/1989 | Smith | |
| 4,888,012 A | 12/1989 | Horn | |
| 4,892,543 A | 1/1990 | Turley | |
| 4,932,966 A | 6/1990 | Christie et al. | |
| 4,963,148 A | 10/1990 | Sulc et al. | |
| 4,994,082 A | 2/1991 | Richards et al. | |
| 5,152,788 A | 10/1992 | Isaacson et al. | |
| 5,171,266 A | * 12/1992 | Wiley et al. | 623/6.22 |
| 5,275,623 A | 1/1994 | Sarfarazi | |
| 5,354,335 A | 10/1994 | Lipshitz et al. | |
| 5,443,506 A | 8/1995 | Garabet | |
| 5,476,514 A | 12/1995 | Cumming | |
| 5,489,302 A | 2/1996 | Skottun | |
| 5,496,366 A | 3/1996 | Cumming | |
| 5,522,891 A | 6/1996 | Klaas | |
| 5,562,731 A | 10/1996 | Cumming | |
| 5,607,472 A | * 3/1997 | Thompson | 623/6.13 |
| 5,674,282 A | 10/1997 | Cumming | |
| 5,728,155 A | 3/1998 | Anello et al. | |
| 5,968,094 A | 10/1999 | Werblin et al. | |
| 5,984,962 A | 11/1999 | Anello et al. | |
| 6,013,101 A | 1/2000 | Israel | |
| 6,096,078 A | 8/2000 | McDonald | |

(Continued)

FOREIGN PATENT DOCUMENTS

EP 0 337 390 A2 10/1989

(Continued)

OTHER PUBLICATIONS

John M. Ramocki et al., "Foldable Posterior Chamber Intraocular Lens Implantation in the Absence of Capsular and Zonular Support," *American Journal of Ophthalmology*, vol. 127, pp. 213-216 (Feb. 1999).

(Continued)

*Primary Examiner*—Bruce Snow
*Assistant Examiner*—Cheryl Miller
(74) *Attorney, Agent, or Firm*—Knobbe, Martens, Olson & Bear, LLP

(57) ABSTRACT

An accommodating intraocular lens is disclosed that provides vision accommodation in response to contraction of an eye's ciliary muscle. The intraocular lens includes a deformable elastic dynamic lens having a non-accommodating surface curvature and a lens-shaping member having flexible portions in contact with peripheral edge regions of the dynamic lens for enabling compressive deformation thereof for changing the lens surface curvature to achieve accommodation. The intraocular lens also includes an elastically flexible coil member mounted around the lens-shaping member flexible portions. A first lens-supporting member has a proximal end region that engages the flexible coil member and a second lens-supporting member has a proximal end region connected to the lens-shaping member.

19 Claims, 6 Drawing Sheets

U.S. PATENT DOCUMENTS

| | | | | |
|---|---|---|---|---|
| 6,117,171 | A * | 9/2000 | Skottun | 623/6.37 |
| 6,120,538 | A * | 9/2000 | Rizzo et al. | 623/6.11 |
| 6,176,878 | B1 | 1/2001 | Gwon et al. | |
| 6,197,058 | B1 | 3/2001 | Portney | |
| 6,197,059 | B1 | 3/2001 | Cumming | |
| 6,200,342 | B1 | 3/2001 | Tassignon | |
| 6,217,612 | B1 | 4/2001 | Woods | |
| 6,231,603 | B1 | 5/2001 | Lang et al. | |
| 6,280,471 | B1 | 8/2001 | Peyman et al. | |
| 6,423,094 | B1 | 7/2002 | Sarfarazi | |
| 6,488,708 | B1 | 12/2002 | Sarfarazi | |
| 6,503,276 | B1 | 1/2003 | Lang et al. | |
| 6,730,123 | B1 * | 5/2004 | Klopotek | 623/6.22 |
| 6,930,838 | B1 * | 8/2005 | Schachar | 359/676 |
| 2001/0001836 | A1 | 5/2001 | Cummings | |
| 2001/0012964 | A1 | 8/2001 | Lang et al. | |
| 2002/0068971 | A1 | 6/2002 | Cummings | |
| 2002/0072795 | A1 | 6/2002 | Green | |
| 2002/0116060 | A1 | 8/2002 | Nguyen et al. | |
| 2002/0143395 | A1 | 10/2002 | Skottun | |
| 2002/0188351 | A1 | 12/2002 | Laguette | |
| 2002/0193876 | A1 | 12/2002 | Lang et al. | |
| 2003/0060878 | A1 * | 3/2003 | Shadduck | 623/6.13 |
| 2003/0109925 | A1 | 6/2003 | Ghazizadeh et al. | |

FOREIGN PATENT DOCUMENTS

| | | |
|---|---|---|
| EP | 0 356 050 | 2/1990 |
| EP | 0 336 877 B1 | 10/1993 |
| WO | WO 84/04449 | 11/1984 |
| WO | WO 96/35398 | 11/1996 |
| WO | WO 99/20206 | 4/1999 |
| WO | WO 00/27315 | 5/2000 |
| WO | WO 00/61036 | 10/2000 |
| WO | WO 00/66037 | 11/2000 |
| WO | WO 01/34067 | 5/2001 |

OTHER PUBLICATIONS

Rana Altan-Yaycioglu et al., "Pseudo-accommodation with Intraocular Lenses Implanted in the Bag," *Journal of Refractive Surgery*, vol. 18, pp. 271-275 (May/Jun. 2002).

Michael Küchle et al., "Implantation of a New Accommodative Posterior Chamber Intraocular Lens," *Journal of Refractive Surgery*, vol. 18, pp. 208-216, (May/Jun. 2002).

Tsutomu Hara et al., "Accommodative Intraocular Lens with Spring Action Part 1. Design and Placement in an Excised Animal Eye," *Ophthalmic Surgery*, vol. 21, pp. 128-133 (Feb. 1990).

Zadno-Azizi, Gholam, et al., U.S. Appl. No. 10/020,853, filed Dec. 11, 2001, entitled "Accommodating Intraocular Lens System," in 45 pages and drawings in 47 pages, with a list of currently pending claims in 8 pages.

Portney, Valdemar, et al., U.S. Appl. No. 10/635,423, filed Aug. 6, 2003, entitled "Accommodating Intraocular Lens with Enhanced Range of Motion," in 16 pages and drawings in pages, with a list of currently pending claims in 2 pages.

PCT International Search Report dated Aug. 19, 2003 in 10 pages.

\* cited by examiner

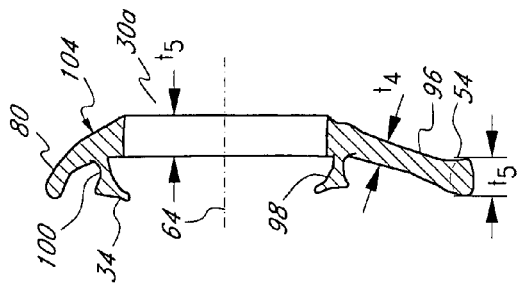
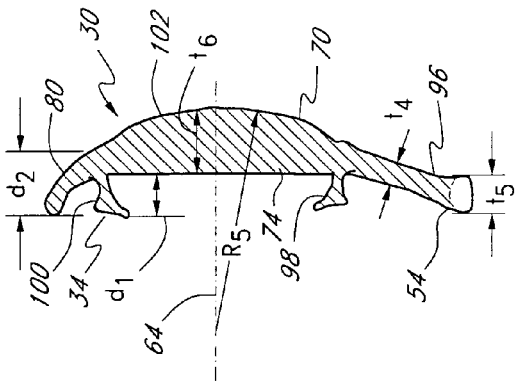
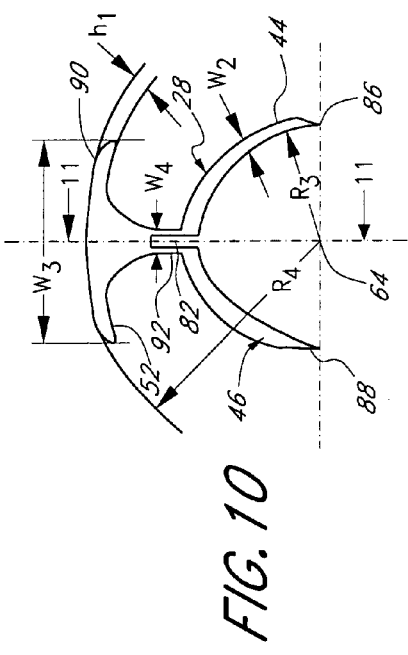
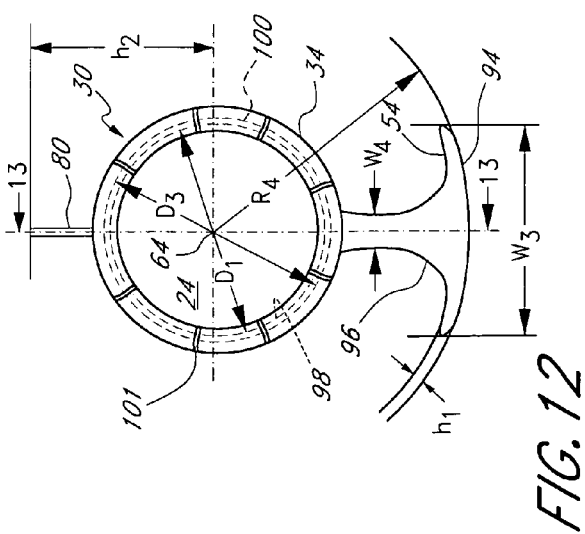

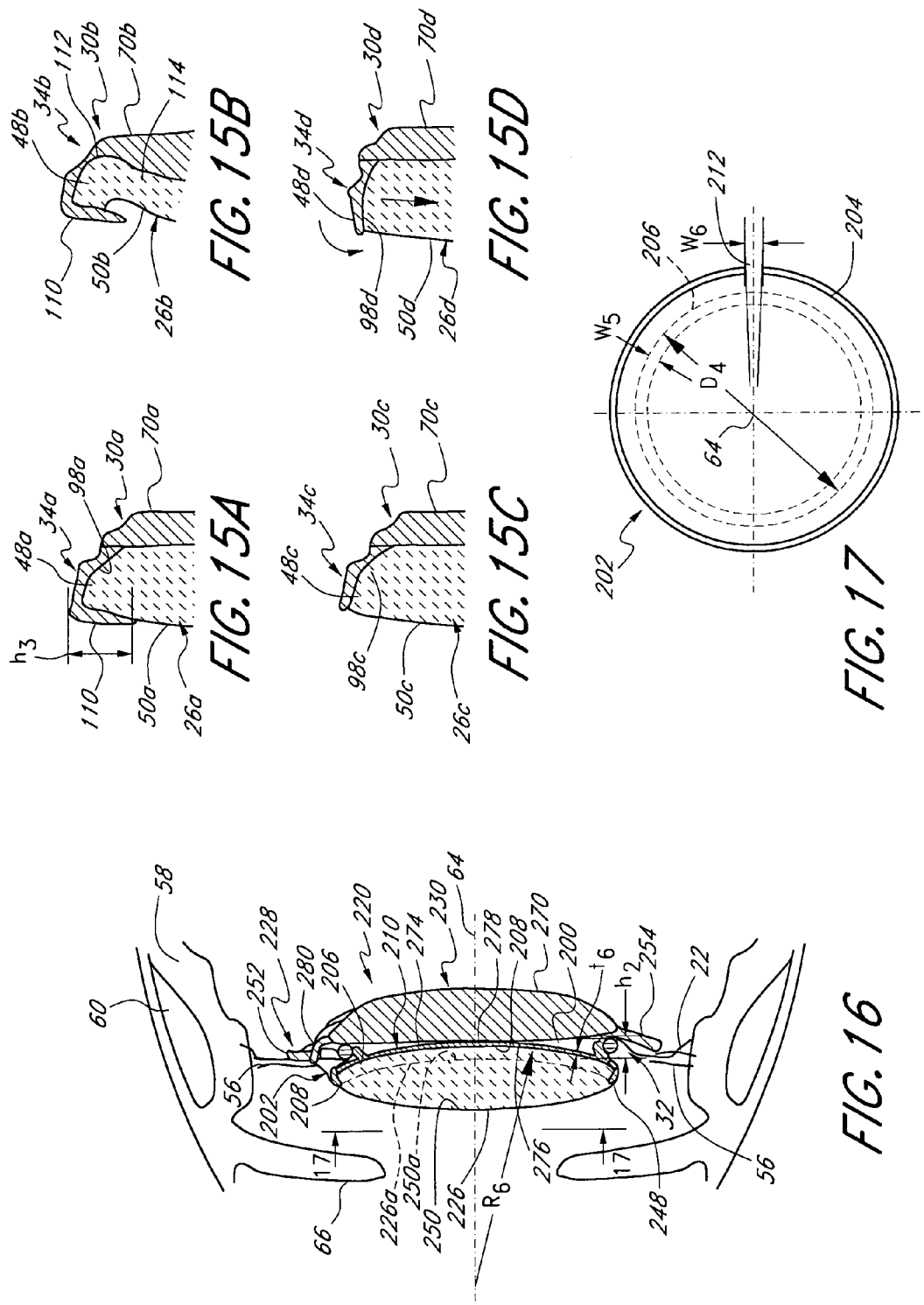

ACCOMMODATING INTRAOCULAR LENS

BACKGROUND OF THE INVENTION

1. Field of the Invention

The present invention relates generally to the field of ophthalmics, more particularly to ophthalmic devices, still more particularly to ophthalmic devices known as intraocular lenses (IOLs), and especially to accommodating intraocular lenses.

2. Background Discussion

At the onset it may helpful to the understanding of the present invention to define the terms "phakic" and "aphakic" as related to human eyes. The term "phakic" is applied to an eye in which the natural ocular lens is still present. This is in contrast to an "aphakic" eye from which the natural ocular lens has—for any reason—been removed. A phakic eye is considered a dynamic or active eye because the living natural lens is subject to change over time, while an aphakic eye is considered a static eye because the natural lens has been removed.

Vision in a normal, healthy eye is enabled by light from a viewed object being refracted to the retina in turn by the cornea and the natural lens located rearwardly of the cornea. An important function of the natural lens, through a process of ciliary muscle contraction and zonular relaxation, is the providing of accommodation, that is, the ability of the elastic natural lens to change its curved shape to enable the eye to focus on objects at distances from near to far in response to the eye and brain sensing an out-of-focus image.

A relatively common ocular problem is impaired or complete loss of vision due to the natural ocular lens becoming cloudy or opaque—a condition known as cataract. The formation of cataracts is typically age related, most individuals over the age of about 60 years suffering from cataracts at least to some extent.

Cataracts cannot currently be cured, reversed, or even significantly arrested. Accordingly, treatment of cataracts involves surgically removing the natural lens when the lens becomes so cloudy that vision is greatly impaired, the result being that a phakic eye becomes an aphakic eye. After a defective natural lens has been surgically removed, the current vision-restoring practice (since about the 1940's) is to implant in the aphakic eye an artificial refractive lens called an intraocular lens (IOL). Previously, thick, heavy, high diopter spectacles were prescribed for aphakic eyes. However, most patients dislike such spectacles because of their uncomfortable weight and unattractive appearance.

Although the implanting of an IOL can generally restore vision in an aphakic eye, corrective spectacles or contact lenses are still usually required for near or far vision, depending upon whether the implanted IOL is selected for far or near vision. This is because, to the knowledge of the present inventor, IOLs providing accommodation comparable to that of a natural healthy lens have not heretofore been available; although, the development of accommodating IOLs has been widely sought.

In addition to the desirability of implanting accommodating IOLs in aphakic eyes in place of the removed natural lens, the implanting of accommodating IOLs would be advantageous in phakic eyes in which the intact natural lens, while still otherwise clear, has lost all or much of its accommodating properties, for example, by becoming less flexible. Nevertheless, the ciliary muscle, which normally functions to provide accommodation of the natural lens generally, remains active for most of an individual's life.

Efforts toward developing accommodating IOLs have relied upon axial IOL movement in the eye and/or IOL lens surface shape change to create dynamic change in ocular power and thus provide accommodation.

Axial movement of implanted IOLs in the eye to provide accommodation is disclosed, for example, in U.S. Pat. Nos. 5,476,514; 5,496,366; 5,674,282 and 6,197,059 to Stuart Cumming. Difficulties associated with axial IOL movement to provide accommodation are due both to the extremely limited ocular space for axial IOL movement that limits the achievable diopter variation necessary for full accommodation, and to satisfactory ocular mechanisms for causing such axial IOL movement.

On the other hand, lens surface shape changing, exemplified in the disclosures of U.S. Pat. Nos. 4,842,601; 4,888,012; 4,932,966; 4,994,082; 5,489,302 have required a spherical lens shape to interact with the rim of ciliary muscle in more then one meridian or even from all 360° orientations. This requires perfect lens centration in regard to the ciliary rim and equal interaction from all meridians; otherwise, absence of central symmetry leads to unequal lens surface curvature in different meridians with resulting reduction in image quality.

Because of these and other problems, a principal objective of the present invention is to provide an improved, surface shape changing accommodating IOL that relies on the interaction with the ciliary muscle in only one meridian. Such improved surface shape changing IOLs may be configured for implanting in aphakic eyes or may alternatively configured for implanting in phakic eyes.

SUMMARY OF THE INVENTION

In accordance with the present invention, there is provided an accommodating intraocular lens for implanting in an individual's eye. The accommodating intraocular lens comprises a deformable elastic dynamic lens, which is preferably formed from a silicone or acrylic material, having a non-accommodating surface curvature and a lens-shaping member having flexible portions in contact with peripheral edge regions of the dynamic lens for enabling deformation of the lens for changing the lens surface curvature.

Included in the accommodating intraocular lens are an elastically flexible member, which may be constructed from a shape memory metallic alloy, in contact with the lens-shaping member flexible portions and first and second lens-supporting members. The first lens-supporting member has a proximal end region engaging the flexible member and the second lens-supporting member has a proximal end region connected to the lens-shaping member. A distal end region of at least the first lens supporting member is shaped for engaging, upon implanting the intraocular lens in an individual's eye, regions of the individual's eye that are responsive to contraction and relaxation of a ciliary muscle disposed in a ciliary body region of the individual's eye.

Preferably, the first and second lens supporting members are configured so their respective distal end regions are aligned with generally opposite regions of the ciliary body when the intraocular lens is implanted in the individual's eye. Also preferably each of the first and second lens supporting members are relatively rigid as compared with the dynamic lens, preferably being formed as is the lens shaping member from polymethyl methacrylate, with the second lens supporting member being rigidly connected to the lens-shaping member or the two may be constructed in one piece. The elastically flexible member is formed in a coil to encircle the flexible portions of the lens-shaping member.

The second lens supporting member may include a static, non-accommodating lens having an optical axis aligned with an optical axis of the dynamic lens.

In one embodiment, the intraocular lens is implanted in an individual's capsular bag from which a natural lens has been removed with the distal end regions of the first and second lens supporting members are configured for direct contact with the ciliary body. Correspondingly, the elastically flexible member and the flexible portion of the lens-shaping member each have a larger diameter unstressed condition and a smaller diameter stressed condition, and are configured for elastically returning to the larger diameter, unstressed conditions, thereby enabling the outer diameter of the dynamic lens to elastically expand to its non-accommodating condition, in response to the reduction of the compressive force applied to distal ends of the first and second lens support members by the ciliary body when the ciliary muscle relaxes.

Moreover, the elastically flexible member is constructed for tightening and squeezing the flexible portions of the lens-shaping member, thereby reducing the outer diameter of the dynamic lens by the lens-shaping member and increasing the surface curvature of the dynamic lens for achieving accommodation, in response to a compressive force applied to distal ends of the first and second lens support members by the ciliary body when the ciliary muscle contracts.

In another embodiment, the intraocular lens is implanted in an individual's capsular bag from which a natural lens has been removed with the distal ends of the first and second lens supporting members being configured for attachment to the capsular bag adjacent opposing ciliary body-connected zonules. In which case, the elastically flexible member is configured for being pulled to a larger diameter, stressed condition and the flexible portions of the lens-shaping member is configured for elastically returning to a larger diameter, unstressed condition, thereby enabling the outer diameter of said dynamic lens to attain its unstressed, non-accommodating condition, in response to an increase in tension applied to distal end regions of the first and second lens supporting members by the zonules when the ciliary muscle relaxes.

Correspondingly, the elastically flexible member is constructed for elastically contracting from the larger diameter stressed condition to a smaller diameter unstressed condition, thereby squeezing the flexible portions of the lens-shaping member to a smaller diameter stressed condition and reducing the outer diameter of the dynamic lens and increasing the surface curvature for achieving accommodation, in response to a release of tension applied to distal end regions of the first and second lens supporting members by the zonules when the ciliary muscle contracts.

In another embodiment, the intraocular lens is implanted in an anterior chamber of an individual's eye, with the distal end region of the first lens supporting member is configured for bearing against the ciliary body and with the second lens supporting member being configured for attaching to an iris region of the eye. The elastically flexible member and the flexible portion of the lens-shaping member each have a larger diameter unstressed condition and a smaller diameter stressed condition and are configured for elastically returning to the larger diameter, unstressed conditions, thereby enabling the outer diameter of the dynamic lens to elastically expand to its non-accommodating condition, in response to the reduction of the compressive force applied to the distal end region of the first lens supporting member by the ciliary body when the ciliary muscle relaxes. In such case, the elastically flexible member is constructed for tightening and squeezing the flexible portions of the lens-shaping member, thereby reducing the outer diameter of the dynamic lens by the lens-shaping member and increasing the surface curvature of the dynamic lens for achieving accommodation, in response to a compressive force applied to the distal end region of the first lens supporting member by the ciliary body when the ciliary muscle contracts.

BRIEF DESCRIPTION OF THE DRAWINGS

The present invention can be more readily understood by a consideration of the following detailed description when taken in conjunction with the accompanying drawings, in which:

FIG. 10 is a front view of the dynamic haptic of FIGS. 1–4, showing its wishbone shape and showing other features of the dynamic haptic;

FIG. 11 is a vertical cross sectional view taken along line 11—11 of FIG. 10 showing additional features of the dynamic haptic;

FIG. 12 is a front view of the static haptic of FIGS. 1–4, showing its shape and showing other features of the static haptic;

FIG. 13 is a vertical cross sectional view taken along line 13—13 of FIG. 12 showing an integral static lens and additional features of the static haptic;

FIG. 14 is a vertical cross sectional view corresponding generally to FIG. 13 of a variation static haptic that is formed as an annular frame without a static lens;

FIG. 15 is a series of enlarged drawings of variations of shape of a dynamic lens confining peripheral edge rim or flange of the static haptic: FIG. 15A showing a first rim shape, FIG. 15B showing a second rim shape, FIG. 15C showing a third rim shape, FIG. 15D showing a fourth rim shape;

FIG. 16 is a vertical cross sectional view corresponding to FIG. 2, of a first variation accommodating intraocular lens in a non-accommodating condition, showing a dynamic lens installed in a shape-changing lens support member that causes both the anterior and posterior surfaces of the dynamic lens to change surface curvature for accommodation;

FIG. 17 is a view looking along line 17—17 of FIG. 16 showing a wedge-shaped cutout the shape-changing lens support member that enables compression of the member;

In the various FIGS., the same elements and features are given the same reference numbers. In the various variation, corresponding elements and features are given the same reference numbers as first set forth, followed by an "a", "b", "c", and so on, as appropriate and/or as will otherwise be evident in the following DESCRIPTION.

DESCRIPTION OF THE PREFERRED EMBODIMENT

Figure 1:
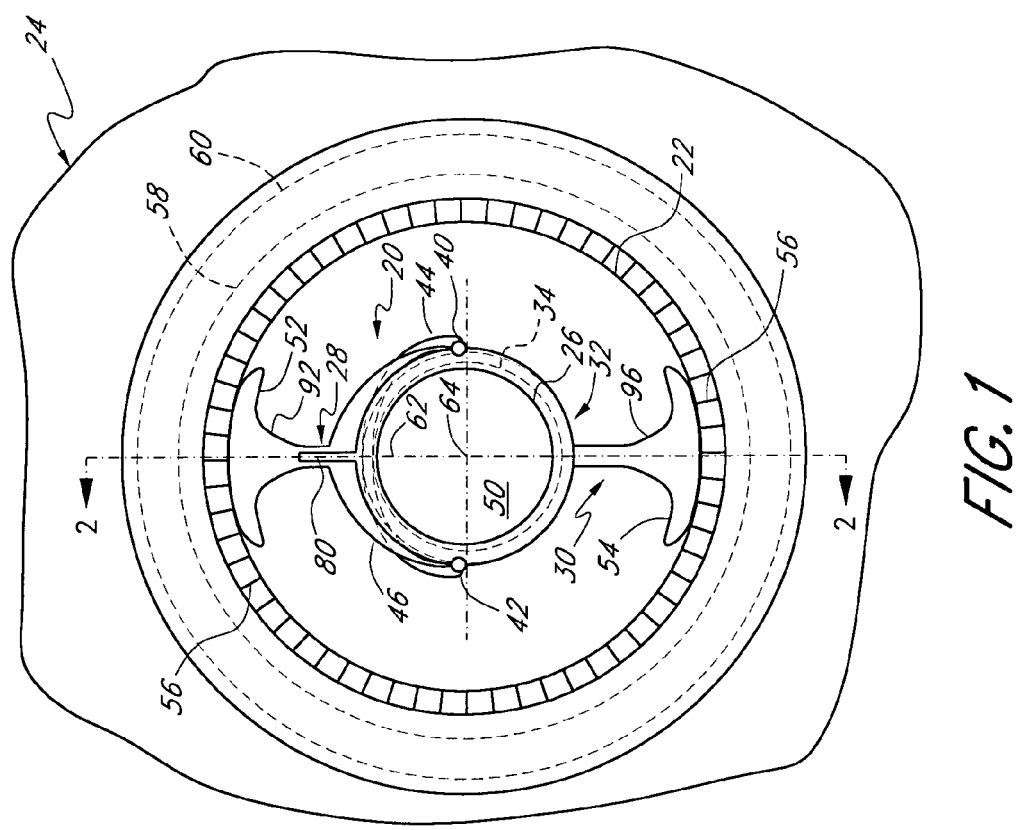
FIG. 1 is a front view of an aphakic accommodation intraocular lens of the present invention implanted in the crystalline lens capsule (capsular bag) of an aphakic eye, showing the accommodating intraocular lens in its unaccommodating condition in which the ciliary muscle in the ciliary body is in its relaxed state that creates tension in the zonules attached to the capsule, and showing an elastically deformable dynamic lens supported in the lens capsule by a static haptic and a dynamic haptic, showing haptic-engaged regions of the capsular bag connected by zonules to the surrounding ciliary body on a single meridian that passes through an optical axis of the dynamic lens, and showing ends of a wishbone-shaped region of the dynamic haptic connected to opposite side regions of a lens compressing spring coil disposed around the periphery of the lens and showing the spring coil in its stressed state thereby releasing the dynamic lens to its unstressed, non-accommodating state.

There is shown in plan view in FIG. 1, an aphakic accommodating intraocular lens (AIOL) 20 in accordance with the present invention. AIOL 20 is depicted in its non-accommodating condition, as described below, implanted in a collapsed crystalline lens capsule or capsular bag 22 of a human eye designated generally by reference number 24.

Comprising AIOL 20, as more particularly described below, is an elastically deformable dynamic, accommodating lens 26, the anterior surface curvature of which is changed in the manner described below to provide vision accommodation of the AIOL. Further comprising AIOL 20 are a first lens supporting member or dynamic haptic 28, a second lens supporting member or static haptic 30 and an elastically flexible dynamic lens spring coil or member 32 (FIG. 2).

Figure 2:
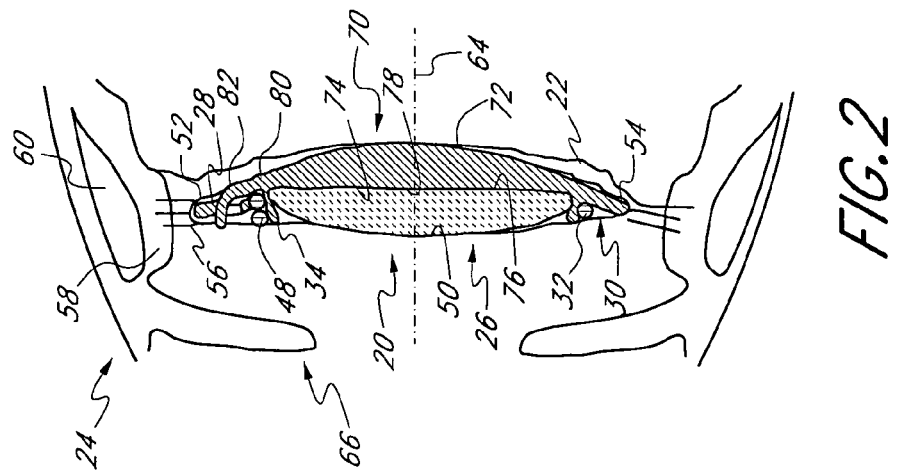
FIG. 2 is a vertical cross sectional view taken along line 2—2 of FIG. 1 showing a static lens that forms part of the static haptic and showing the lens compressing spring coil supported on a peripheral flange region of the static lens portion of the static haptic that also surrounds the periphery of the dynamic lens, and also showing a guide portion of the static haptic that extends through a movement-limiting slot in the dynamic haptic.

Dynamic lens 26, which is shown in FIG. 2, by way of example, as a plano-convex lens, is supported on static haptic 30 within a thin, flexible peripheral rim or portion 34 of static haptic 30 and around which is installed spring coil 32 that is shown in its expanded, stressed state. Considering flexible rim or portion 34 within which dynamic lens 26 is received for lens shaping, static haptic 30 may be considered as a lens-shaping member. Sidewardly projecting ends 40 and 42 of spring coil 32 are connected to ends of opposite legs 44 and 46 of dynamic haptic 28.

As described below relative to FIGS. 3 and 4, the releasing of spring coil 32 from its stressed state by first, dynamic haptic 28, in response to contraction of ciliary muscle 60 and consequent reduced tension in zonules 56 connected to capsular bag 22, results in a returning of the spring coil towards its unstressed diameter. This diameter reduction of spring coil 32 causes radial squeezing (through static haptic flexible rim 34) of a peripheral edge 48 of dynamic lens 26, resulting in an increased curvature of a curved anterior surface 50 of the dynamic lens 26 to provide visual accommodation for near viewing.

Arcuate foot regions 52 and 54, respectively, of dynamic haptic 28 and static haptic 30 are anchored in capsular bag 22 and are thereby operatively connected by zonules 56 (which are connected to the periphery of the capsular bag) to a ciliary body 58 containing a ciliary muscle 60 that is depicted in its relaxed, non-accommodating state in FIG. 2. Such anchoring of haptic feet 52 and 54 may be accomplished by cell growth resulting from ocular immobility chemically induced for several days. As depicted in FIG. 1, haptic foot regions 52 and 54 are centered on a single meridian 62 that passes through an optical axis 64 of lens 26. An iris 66 is shown in FIG. 2 but is omitted in FIG. 1 for clarity reasons.

Shown in FIG. 2, by way of example with no limitation being thereby intended or implied, static haptic 30, which, as described above, confines accommodating lens 26 within flexible peripheral rim or flange 34, incorporates a fixed, static or non-accommodating lens 70. Static lens 70 is depicted as a plano-convex lens aligned along optical axis 64. Static lens 70 has a curved posterior surface 72 and a flat anterior surface 74 that abuts a flat posterior surface 76 of dynamic lens 26.

It is, however, to be appreciated that dynamic lens 26 and/or static lens 70 may alternatively be formed as plano-convex lenses or meniscus (concave-convex) lenses (not shown), according to desired optical power to be provided by AIOL 20. By way of example, with no limitation being thereby implied or intended, dynamic lens 26 and static lens 70 in combination may be configured to provide between about −25 diopter and about +35 diopter correction. As depicted in FIG. 2, dynamic lens 26 may be laser tacked to static lens 70 at a point 78 at respective abutting surfaces 76 and 74 on optical axis 64 (FIG. 2) to assist in the confining of the dynamic lens in static haptic 30.

Formed as part of static haptic 30 is a slender, curved guide element 80 (FIG. 2) that extends upwardly and forwardly from an upper region of static lens 70. Static haptic guide element 80 extends forwardly through a narrow slot 82 generally centrally located in dynamic haptic 28 adjacent foot 52 (FIG. 1) to provide a radially sliding connection between static haptic 30 and the dynamic haptic.

It will be appreciated that when ciliary muscle 60 in its relaxed state tension is created in zonules 56. Such zonule tension in pulls on haptics 28 and 30, thereby pulling spring coil 32 to its open, stressed state, thereby permitting dynamic lens 26 to resume its unstressed, non-accommodating, flatter state due to dynamic lens elasticity and the flexibility of static haptic rim 34.

Figure 4:
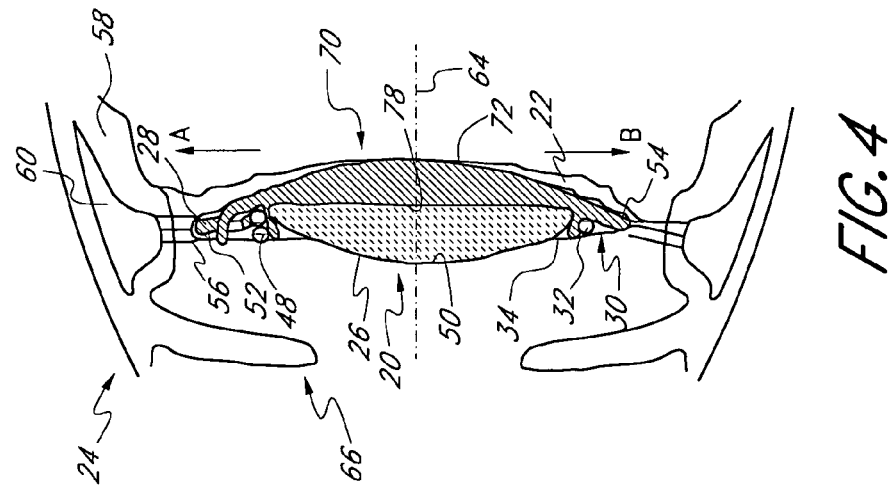
FIG. 4 is a vertical cross sectional view taken along line 4—4 of FIG. 3, similar to the cross sectional view of FIG. 2, showing the accommodating intraocular lens in its accommodating condition.
Figure 3:
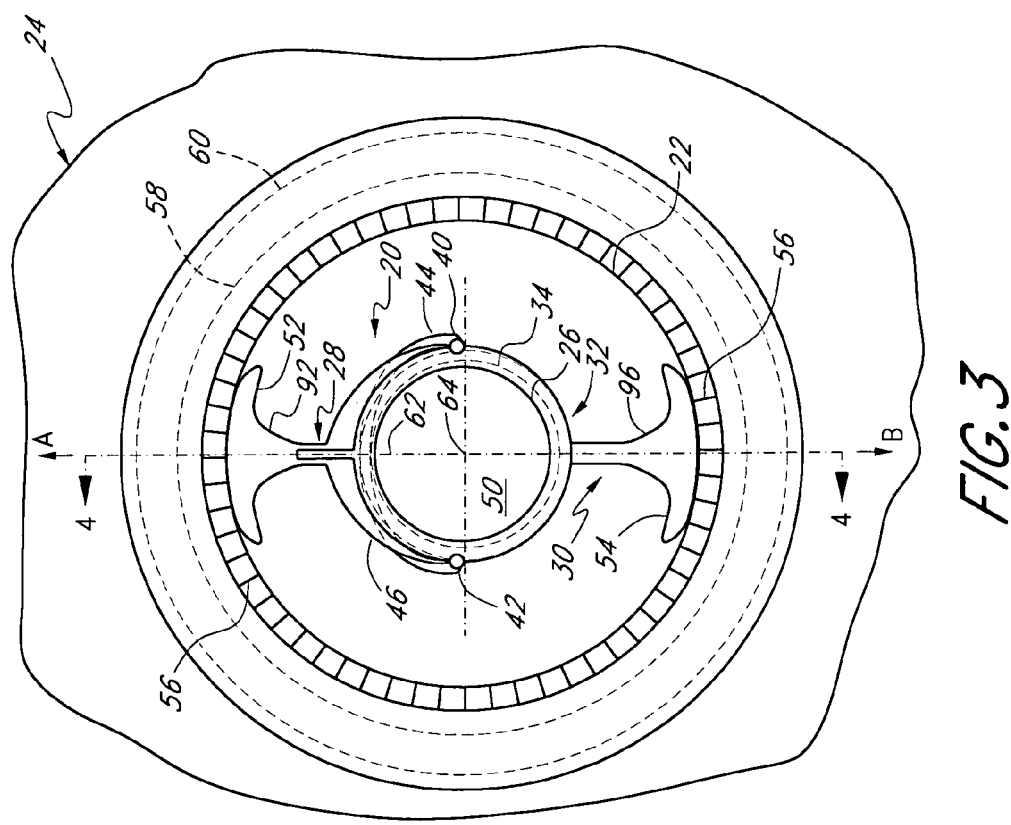
FIG. 3 is a front view of the aphakic accommodating intraocular lens of FIG. 1, showing the dynamic haptic in its accommodating condition in which the ciliary muscle is in its contracted state thereby releasing tension in the zonules and enabling the lens compressing spring coil to return from its stressed state to its unstressed state that causes radial compression of the dynamic lens, thereby increasing its anterior surface curvature for near object viewing.

FIGS. 3 and 4 correspond respectively to FIGS. 1 and 2 but depict AIOL 20 in its accommodating condition rather than in its non-accommodating condition. In response to ciliary muscle 60 (FIG. 4) being activated by eye 22 to its contracted state, tension in zonules 60 is relaxes, thereby releasing tension on dynamic and static haptics 28 and 30. This permits spring coil 32 (which is connected to dynamic haptic 28) to return toward (or to) its smaller diameter, unstressed state from its stressed state depicted in FIG. 1, thereby applying a compressive force, through static haptic flexible rim 34, to dynamic lens peripheral edge 48. The applying of a compressive force to dynamic lens peripheral edge 48 causes the curvature of dynamic lens anterior surface 50 to increase to the extent needed to focus eye 24 on closer objects. In that manner, AIOL 20 provides accommodation in the same way as the natural lens that is replaced by the AIOL.

As described above, when ciliary muscle 60 then relaxes, the resulting increased zonule tension pulls dynamic haptic 28 radially outwardly (direction of Arrow A, FIGS. 3 and 4) and static haptic 30 radially outwardly (direction of Arrow B) thereby stretching spring coil 32 toward its stressed, larger diameter state depicted in FIG. 1. This enables the elastic restoring action of dynamic lens 26 and flexibility of static haptic rim 34 to return the dynamic lens toward its flatter unstressed condition or state. This automatic restoring action results in decreasing the previously increased curvature of dynamic lens anterior surface 50 to the extent needed to focus eye 24 on more distant objects.

Figure 5:
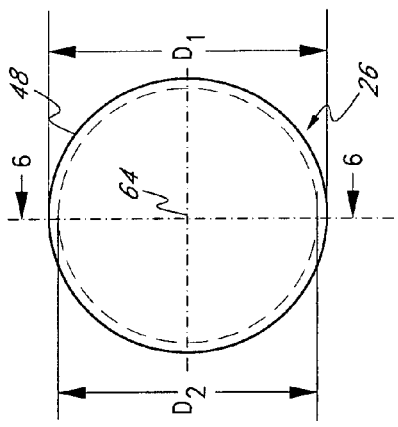
FIG. 5 is a front view of the dynamic lens of FIGS. 1–4, showing the lens in its unstressed, flatter non-accommodating state and showing in phantom lines the lens in its stressed, more curved accommodating state.

FIG. 5 depicts in solid lines dynamic lens 26 in its flatter, unstressed, non-accommodation condition of FIGS. 1 and 2, and depicts in phantom lines the lens in its more rounded stressed accommodating condition of FIGS. 3 and 4. In its unstressed, non-accommodating condition, dynamic lens 26 has an outside diameter, $D_1$, that may, for example, be about 6.1 mm (millimeters); in its stressed, accommodating condition, dynamic lens 26 has an outside diameter, $D_2$, that may, for example, be about 5.6 mm.

Figure 6:
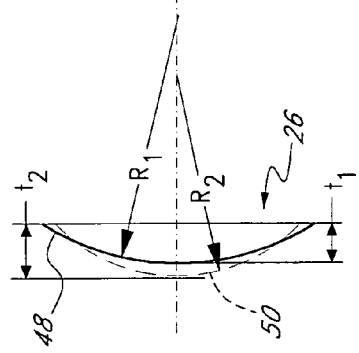
FIG. 6 is a vertical cross sectional view taken along line 6—6 of FIG. 5 showing features of the dynamic lens in its unstressed non-accommodating state and showing in phantom lines the lens in its stressed accommodating state.

As shown in the cross section of FIG. 6, dynamic lens 26 may, for example, have an unstressed, non-accommodating center thickness, $t_1$, of about 1.2 mm and a stressed, accommodating center thickness, $t_2$, of about 1.4 mm. Dynamic lens anterior surface 50 may, for example, have a corresponding unstressed, non-accommodating radius of curvature, $R_1$, of about 7.0 mm and a stressed, accommodating radius of curvature, $R_2$, of about 6.0 mm. Dynamic lens 26 may be constructed, for example, by cast molding, from an elastomeric silicone or acrylic material having an index of refraction of about 1.4 or greater. It will be appreciated that dynamic lens 26 may be constructed having a varying stiffness profile from optical axis 64 to lens periphery 48 to assist the uniform curvature change of lens surface 50 during the lens accommodation process.

Figure 7:
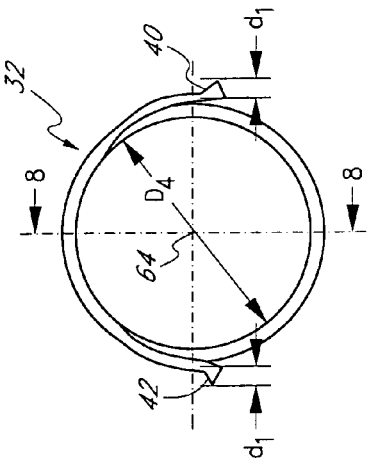
FIG. 7 is a front view of the lens compressing spring coil of FIGS. 1–4, showing the spring coil in its in its unstressed state.

FIG. 7 depicts compression spring coil 32, which is preferably formed in 1½ circular coils, in its smaller inside diameter, unstressed state (depicted in FIGS. 3 and 4) having a preferred inside diameter, $D_4$, of about 6.0 mm and a thickness, $t_3$, of preferably about 0.25 mm. Coil ends 40 and 42, which are formed at 90 degree angles, may extend radially outwardly distances, $d_1$, of about 0.5 mm, and are formed having holes (not shown) for receiving connecting ends of haptic legs 44 and 46. Spring coil 32 is preferably constructed from an elastically flexible, shape memory spring alloy such as Nitinol or Elgiloy.

Figure 9:
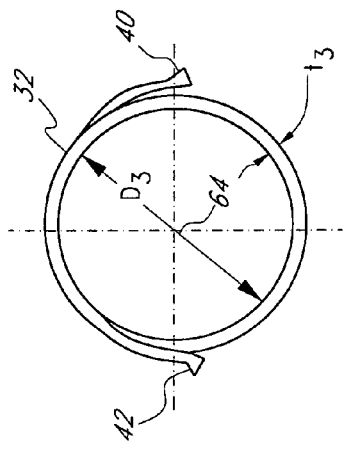
FIG. 9 is a front view of the lens compressing spring coil similar to FIG. 7, but showing the spring coil in its in its stressed state.
Figure 8:
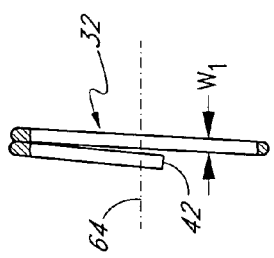
FIG. 8 is a vertical cross sectional view taken along line 8—8 of FIG. 7 showing features of the lens compressing spring coil in its un stressed state.

As shown in FIG. 8, coil 32 has a width, $w_1$, that is preferably between about 0.2 mm and about 0.5 mm. Coil 32 is depicted in FIG. 9 in its larger inside diameter stressed state of FIGS. 1 and 2, having an inside diameter, $D_3$, which is preferably about 6.5 mm.

First, dynamic haptic 28 is depicted in plan view in FIG. 10, as being generally wishbone or saddle shaped with arcuate legs 44 and 46 having a preferred inner radius, $R_3$, of about 3.3 mm from optical axis 64 and nominal widths, $w_2$, of about 0.3 mm. Respective distal ends 86 and 88 of haptic legs 44 and 46 taper to spring coil attachment points. Foot 52 of dynamic haptic 28 preferably has a height, $h_1$, and a width, $w_3$, along an arc of radius, $R_4$, on which a radially outward surface 90 of the foot lies. Preferably, foot height, $h_1$, is about 0.3 mm; width, $w_3$, is about 7.0 mm; and radius, $R_4$, from axis 64 is about 4.6 mm. A slender haptic neck region 92 interconnecting foot 52 and legs 44 and 46, and in which guide slot 82 is formed, has a preferred width, $w_4$, of about 1.0 mm.

Shown in cross section in FIG. 11, dynamic haptic foot 52 has a preferred thickness, $t_5$, of about 0.3 mm. Slot 82 in neck region 92 has a preferred length, $l_1$, of about 0.7 mm and representative haptic leg 46, along with neck region 92 has a preferred thickness, $t_4$, of about 0.3 mm.

Dynamic haptic 28 is preferably constructed from a material, for example, polymethyl methacrylate (PMMA), that is stiffer than that from which dynamic lens 26 is constructed. At least foot 52 and neck region 92 may be roughened or provided with small holes (not shown) to assist cell growth anchoring of the haptic inside capsular bag 22.

Second, static haptic 30 is depicted in FIGS. 12 and 13. As shown in FIG. 12, static haptic foot 54 is preferably the same size and shape as above-described foot 52 of dynamic haptic 28, a radially outer foot surface 94 being on an arc of the same radius $R_4$ and foot 54 having the same height, $h_1$, width, $w_3$, and thickness $t_5$ (FIG. 13). A static haptic neck region 96 that joins foot 54 to static lens 70 is preferably sized the same as above-described dynamic haptic neck region 92 (except for slot 82), having the same width, $w_4$, (FIG. 12) and thickness $t_4$ (FIG. 13). At least foot 54 and neck region 96 may be roughened or provided with small holes (not shown) to assist cell growth anchoring of the haptic inside capsular bag 22.

As shown in FIG. 13, haptic flexible rim or portion 34 extends parallel to optical axis 64 from flat surface 70 a distance, $d_1$, that is preferably about 0.4 mm. Rim 34, as seen in cross section, has a recessed inner annular surface groove 98 for receiving and retaining peripheral edge 48 of dynamic lens 26, and has a recessed outer annular surface groove 100 for receiving and retaining spring coil 32. Inner surface groove 98 has a diameter, $D_1$, equal to outer, unstressed diameter, $D_1$, of dynamic lens 26 (FIG. 5) and outer surface groove has a diameter, $D_3$, equal to inner, unstressed diameter, $D_3$, of spring coil 32 (FIG. 7).

As shown in FIG. 12, rim 34 is formed having a number of radial notches 101 equally spaced around the rim in order to enhance rim flexibility and enable the rim to be squeezed to a smaller diameter by action of spring coil 32 in the dynamic lens accommodating process described above.

Preferred static, non-accommodating lens 70 may have a center thickness, $t_6$, of about 4.0 mm and a posterior surface 102 may have a radius of curvature, $R_5$, centered on optical axis 64, of about 200 mm (FIG. 13). Guide 80 is angled in the direction of rim 34 a distance, $d_2$, of preferably about 0.5 mm. An overall height, $h_2$, (FIG. 12) of haptic 30 from optical axis 64 to the tip of guide 80 is preferably about 3.9 mm.

It is within the scope of the present invention to provide a variation static haptic 30a (shown in cross section in FIG. 14) that is similar to above-described static haptic 30, but is constructed without a static lens, such as static lens 70 depicted for static haptic 30 in FIG. 13. As such, static haptic 30a comprises an open annular frame 104 that supports above-described rim or flange 34. Annular frame 104, which is connected by neck region 96 to foot 54, has a thickness, $t_5$, that may be about 0.3 mm, or may be the same as thickness $t_4$ of neck region 96 of static haptic 30 (FIG. 13).

Preferably static haptics 30 and 30a are constructed from the same relatively stiff (as compared to dynamic lens 26) material, for example, PMMA, as above-described dynamic haptic 28 is constructed.

FIGS. 15A–15D depict in cross section four static haptic flexible rim or portion variations that may be used to advantage to transmit compressing forces from spring coil 32 to dynamic lens 26. As such, FIGS. 15a–15d correspond generally to corresponding portions of the cross sections of FIGS. 13 and 14.

FIG. 15A depicts a first variation rim 34a formed on a variation static haptic 30a having a radially inwardly directed lip 110, having a height, $h_3$, of about 0.4 mm, that assists in confining peripheral edge 48a of dynamic lens 26a and may thereby help to prevent undesirable lens bulging at its periphery during the above-described lens accommodating process.

FIG. 15B depicts a second variation rim 34b formed on a second variation static haptic 30b also having a radially inwardly directed lip 110, having a height, $h_3$, of about 0.4 mm, that assists in confining peripheral edge 48b of dynamic lens 26b. In this variation, a static lens 70b is shown having a shallow arcuate annular recess 112 into which a corresponding curved peripheral dynamic lens region 114 fits. Again the objective is to help assure uniform curvature change of dynamic lens anterior surface 50b during the lens accommodating process.

FIG. 15C depicts an inner annular surface 98c of a third variation static haptic rim 34c that is more curved than surface 98 of rim 34 depicted in FIGS. 13 and 14 as sometimes may be desired. FIG. 15D depicts a fourth variation static haptic rim 34d that is a compromise between rim 34c depicted in FIG. 15C and rim 34 depicted in FIGS. 13 and 14.

It is to be appreciated, however, that still other configurations of static haptic rim 34 are within the scope of the present invention.

First Variation AIOL of FIGS. 16 and 17:

FIG. 16 is a cross sectional drawing, corresponding to the cross section of FIG. 2, of a first variation aphakic AIOL 220 depicted in a non-accommodating condition (elements and features corresponding to previously described features and elements are given the same reference number as the original elements and features preceded by the digit "2"; newly introduced features and elements are given a new, 200 series number).

AIOL 220, which implanted in capsular bag 22 in the manner of above-described AIOL 20, is shown, by way of example, having a biconvex dynamic lens 226 (shown in solid lines) and alternatively, also by way of illustration, having a concave-convex dynamic lens 220a (shown in broken lines).

A static haptic 228 of AIOL 220 is preferably constructed the same as above-described dynamic haptic 28 of AIOL 20. A static haptic 230 of AIOL 220 is preferably constructed the same as above-described static haptic 30 of AIOL 20, except that static haptic 230 is constructed without a rim or flange corresponding to rim or flange 34 of static haptic 30. In place of a rim or flange corresponding to rim or flange 34 of static haptic 30, AIOL 220 includes a dished flexible, dynamic lens-shaping member 202 that is centrally attached (as by laser tack welding) to static haptic 230 at a point 278 on optical axis 64 and thus can be considered part of the static haptic.

Dynamic lens-shaping member 202 is formed having a radius, $R_6$, which may be about 14 mm centered on optical axis 64. Radius, $R_6$, also defines the radius of posterior surface 276 of dynamic lenses 226 or 226a depending on the lens used in AIOL 220.

Formed around the periphery of lens-shaping member is a dynamic lens retaining rim 204 having an arcuate inner annular surface 208 that has the same diameter as the outside diameter of lenses 226 or 226a, as is above-described for inner annular groove 98 of static haptic rim 34 (FIGS. 12–14). Lens-shaping member 202 is further formed having an annular rib 206 protruding from a posterior surface 210.

As shown in FIG. 17, lens-shaping member rib 206 has an outer diameter, $D_4$, that is the same as the inner diameter of spring coil 32 in its unstressed state (FIG. 17) and has a width, $w_5$, that may be about 0.2 mm. Rib 206 has a height, $h_2$, (FIG. 16) that depends upon the radius of curvature, $R_6$, of lens shaping member 202, being such that the member rests on flat anterior surface 274 of static lens 270. In any event, rib height, $h_2$, is at least the width, $w_1$, of spring coil 32 that is installed onto rib 206. Member 202 is formed, as depicted in FIG. 17, having a wedge shaped slit or cutout 212 with a peripheral width, $w_6$, of about 0.5 mm to enable its reduction in diameter for accommodation of dynamic lens 226 or 226a, as described below. Member 202 preferably has a thickness, $t_6$, (FIG. 16) of about 0.05 mm and is preferably constructed of the same stiff, elastically flexible material as haptics 28, 228 and 30,230.

AIOL 220 provides accommodation in the same manner as above described for AIOL 20 (FIGS. 1–4). In the non-accommodating state of AIOL 220 depicted in FIG. 16, ciliary muscle 60 is in its relaxed state with the result that zonules 56 attached to dynamic and static haptics 228 and 230 are in tension. Such tension pulls spring coil 32 to its stressed more-open state, depicted in FIG. 19, thereby releasing the compressive stress on rib 206 of flexible lens-shaping member 202. This release of compressive stress on member 202 permits the member to expand to its unstressed state and permits dynamic lens 226 (or 226a, as the case may be) to expand from its compressed, accommodating state to its flatter, non-accommodating, normal state by the elastic restoring properties of the lens.

In the accommodation condition for which ciliary muscle 60 is contracted as depicted for AIOL 20 in FIGS. 3 and 4, tension in zonules 56 is relaxed, permitting spring coil 32 to return to its normal uncompressed state depicted in FIG. 17, thereby causing a compressive stress to be applied to lens-shaping member 202, through rib 206. This compressive stress on member 202 applies a compressive force to peripheral edge 248 of dynamic lens 226 (or 226a) causing the dynamic lens to elastically deform to a more rounded, accommodating shape.

Figure 18:
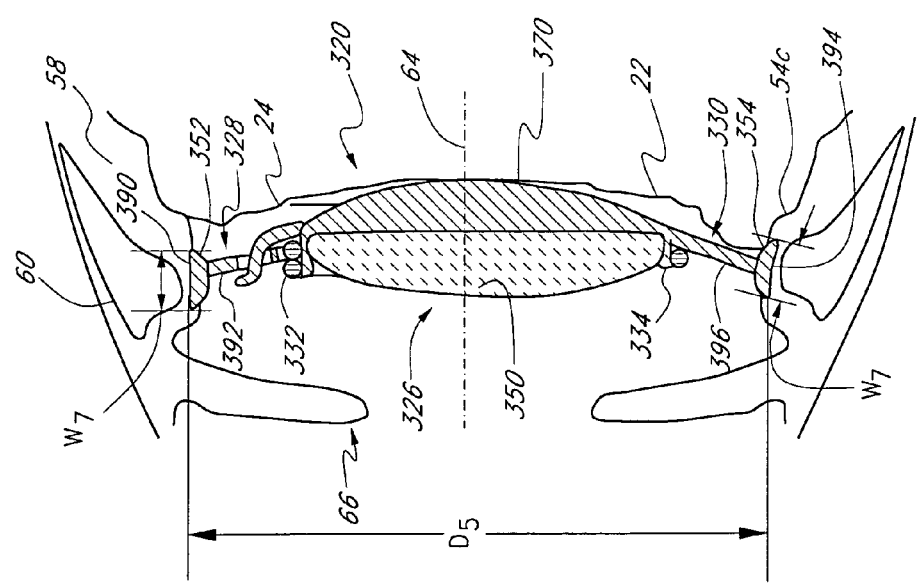
FIG. 18 is a vertical cross sectional view corresponding to FIG. 4, of a second variation accommodating intraocular lens in an accommodating condition, the second variation accommodating intraocular lens being shown as an aphakic lens similar to the aphakic accommodating intraocular lens of FIGS. 1–4 except showing that both a dynamic haptic and a static haptic are directly attached to ciliary body containing the ciliary muscle.

Second Variation AIOL of FIG. 18:

It may in some instances be desirable or necessary to attach an aphakic AIOL implanted in capsular bag 22 directly to ciliary body 58, as depicted in FIG. 18 for a second variation aphakic AIOL 320. As a result, AIOL 320 is responsive for accommodation to compression forces from ciliary body 58, caused by ciliary muscle 60 contraction, rather than from zonular tension relaxation to which above-described AIOL 20 is responsive for accommodation. Elements and features of second variation AIOL 320 that correspond to previously described features and elements of above-described AIOL 20 are given the same reference number as the original elements and features preceded by the digit "3", with newly introduced features and elements being given a new, 300 series number)

FIG. 18, which is a cross sectional drawing of second variation aphakic AIOL 320 in the accommodation condition, corresponds to the FIG. 4 cross section of aphakic AIOL 20 in its accommodation condition. Second variation AIOL 320 is in most respects similar to above-described AIOL 20 except that respective neck regions 392 and 396 of dynamic and static haptics 328 and 330 are made longer to enable associated haptic feet 352 and 354 to bear against ciliary body 58 adjacent capsular bag 22. In this regard, dynamic and static haptics 328 and 330 are constructed so that respective outer surfaces 390 and 394 of haptic feet 352 and 354 are on a diameter, $D_5$, that is about 11.5 mm. Preferably, haptic feet 352 and 354 are made having a width, $w_7$, that is about 1.0 mm to provide a greater ciliary body contact area.

In order for AIOL 320 to provide accommodation in response to compression forces applied to dynamic haptic 328 and static haptic 330 by ciliary body 58 when ciliary muscle 60 contracts, spring coil 332 is, in its normal, non-accommodating, unstressed state made as depicted in FIG. 9 for above-described spring coil 32 in its non-accommodating stressed state. In its stressed, accommodating state, spring coil 332 is as depicted in FIG. 7 for spring coil 32 in its unstressed, accommodating state. Accordingly, responsive to compressive forces from ciliary body 58, dynamic haptic 328 acts on spring coil 332 to compress it from its non-accommodating, unstressed condition to its smaller diameter stressed, accommodating state, thereby decreasing the coil diameter and applying a compressive, accommodating stress, through flexible rim or portion 334 of static haptic 330, to dynamic lens 326.

When ciliary muscle 60 relaxes, the compressive force from ciliary body 58 on dynamic haptic 328 is reduced permitting spring coil 332 to expand to its normal, unstressed state, thereby permitting dynamic lens 326 and static haptic rim 334 to elastically return to their flatter, non-accommodating condition.

It will be appreciated that the dynamic lens configuration described above with respect to FIGS. 16 and 17 may be applied to second variation AIOL 320 instead of the lens configuration depicted in FIG. 18.

Figure 19:
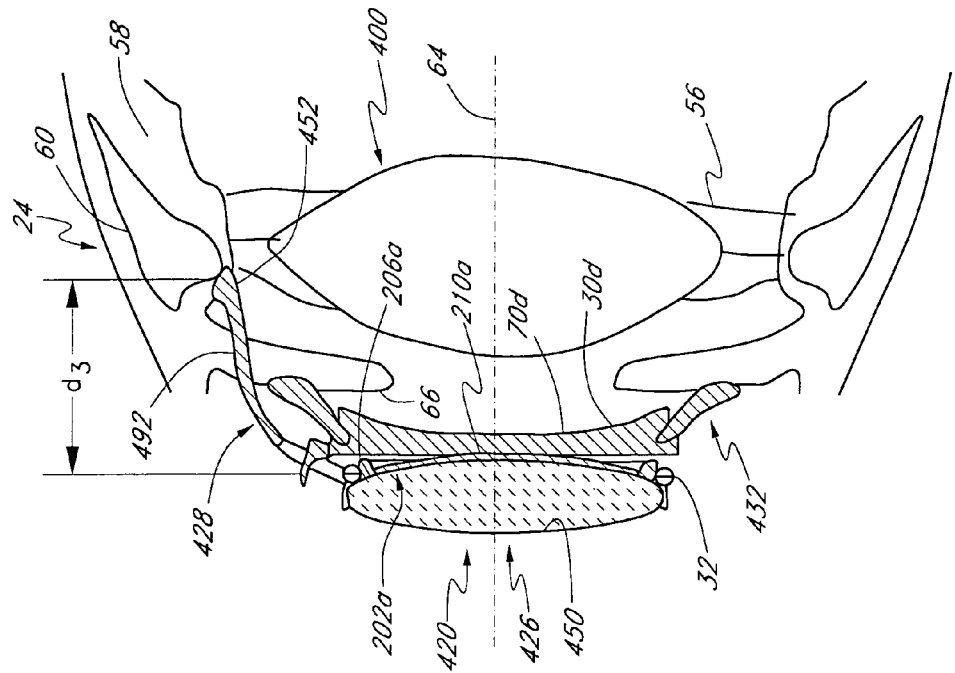
FIG. 19 is a vertical cross sectional view corresponding generally to FIG. 4, of a third variation accommodating intraocular lens, the third variation accommodating intraocular lens being a phakic lens, showing a static haptic fixated to an iris and showing a dynamic haptic directly attached to the ciliary body containing the ciliary muscle.

Third Variation AIOL of FIG. 19:

It may in some instances be desirable to implant an AIOL in a phakic eye, for example, when its natural lens has lost the ability to provide complete or at least substantial accommodation but is otherwise healthy. Accordingly, FIG. 19 depicts, in a cross section corresponding generally to the cross section of FIG. 18, a third variation, phakic AIOL 420 that is fixated to iris 66 and that is responsive in the manner described above for second variation, aphakic AIOL 320 for accommodation to compression forces from ciliary body 58, caused by ciliary muscle contraction.

Third variation, phakic AIOL 420 is depicted in FIG. 19, by way of illustrative example with no limitation being thereby intended or implied, as corresponding in many respects to first variation, aphakic AIOL 220 depicted in FIG. 16. Elements and features of third variation AIOL 420 that correspond to previously described features and elements of above-described AIOL 20 are given the same reference number as the original elements and features preceded by the digit "4", that correspond to previously described features and elements newly introduced relative to above-described first variation AIOL 220 are given the same reference number followed by an "a" and newly introduced features and elements are given a 400 series number.

Shown comprising third variation AIOL 420 are a dynamic haptic 428, a static haptic 430, a dynamic lens 426, a dynamic lens shaping member 202a and a spring coil 32. Dynamic haptic 428 is shaped generally like above-described dynamic haptic 28, except that for being formed having an elongated, curved neck region 492 that provides an offset distance, $d_3$, of about 0.8 mm between haptic foot 452 that engages ciliary body 58 beneath ciliary muscle 60 and spring coil 32. Static haptic 430, shown by way of example as incorporating a plano-concave static lens 270a, is configured as disclosed in my prior U.S. Pat. No. 6,152,959, which is incorporated herein in its entirety by specific reference, for fixation to iris 66 forward of an intact natural lens 400.

Dynamic lens 426, shown by way of example as a biconvex lens is similar to above-described dynamic lens 226 (FIG. 16) and is installed in lens shaping member 202a that is preferably identical to above described lens shape changing member 202.

Accommodation of phakic AIOL 420 is achieved by the compression of spring coil 32 installed around lens shaping member rib 206a in the manner described above for first variation, aphakic AIOL in response to contraction of ciliary muscle 60.

It will be appreciated that the dynamic lens configuration depicted in FIG. 18 may alternatively be used in phakic AIOL 420.

It will also be appreciated that accommodation of both phakic AIOL 420 and aphakic AIOL 220 can be achieved by installing a spring coil, corresponding to spring coil 32 around the inside of lens shaping member rib 206 and 206a instead of around the outside thereof as depicted in respective FIGS. 16 and 19. In such case, accommodation of dynamic lens 226 or 426 is provided by expanding the spring coil diameter in response to contraction of ciliary muscle 60 in a manner evident from the above-disclosures.

Although there have been described above an accommodating intraocular lens and several variations thereof, in accordance with the present invention for purposes of illustrating the manner in which the present invention maybe used to advantage, it is to be understood that the invention is not limited thereto. Consequently, any and all variations and equivalent arrangements that may occur to those skilled in the applicable art are to be considered to be within the scope and spirit of the invention as set forth in the claims that are appended hereto as part of this application.

What is claimed is:

1. An accommodating intraocular lens for implanting in an individual's eye, which comprises:
   a deformable elastic dynamic lens having a surface curvature;

a lens-shaping member having flexible portions in contact with said dynamic lens for enabling deformation of said dynamic lens for changing said surface curvature;

an elastically flexible member in contact with said lens-shaping member flexible portions, wherein said flexible member comprises a coil encircling said flexible portions of the lens-shaping member; and first and second lens supporting members, said first lens supporting member having a proximal end region engaging said flexible member and a distal end region, said second lens supporting member having a proximal end region connected to said lens-shaping member and a distal end region, the distal end region of the first lens supporting member being configured upon implantation to engage a first region of said individual's eye that is responsive to contraction and relaxation of a ciliary muscle disposed in a ciliary body region of said individual's eye.

2. The accommodating intraocular lens as claimed in claim 1, wherein the distal end region of the second lens supporting member is configured to engage a second region of said individual's eye, the first and second regions generally centered on a single meridian that passes through an optical axis of the dynamic lens.

3. The accommodating intraocular lens as claimed in claim 1, wherein each of said first and second lens supporting members are relatively rigid as compared with said dynamic lens.

4. The accommodating intraocular lens as claimed in claim 1, wherein said proximal end region of the second lens supporting member is rigidly connected to said lens-shaping member.

5. The accommodating intraocular lens as claimed in claim 1, wherein said lens-shaping member and said second lens supporting member are constructed in one piece.

6. The accommodating intraocular lens as claimed in claim 1, wherein said intraocular lens is implantable in an individual's capsular bag from which a natural lens has been removed and wherein the distal end regions of said first and second lens supporting members are configured for attachment to the capsular bag adjacent to opposing ciliary body-connected zonules.

7. The accommodating intraocular lens as claimed in claim 6, wherein said flexible portions of the lens-shaping member are responsive to increases of tension applied to said first and second lens supporting members by said zonules upon relaxation of said ciliary muscle by elastically returning to a larger diameter condition, thereby increasing a diameter of said dynamic lens and decreasing said surface curvature to attain a non-accommodating condition.

8. The accommodating intraocular lens as claimed in claim 6, wherein said flexible portions of the lens-shaping member are responsive to decreases of tension applied to said first and second lens supporting members by said zonules upon contraction of said ciliary muscle by elastically returning to a smaller diameter condition, thereby reducing a diameter of said dynamic lens and increasing said surface curvature to attain an accommodating condition.

9. The accommodating intraocular lens as claimed in claim 1, wherein said flexible member comprises a shape memory metallic alloy.

10. The accommodating intraocular lens as claimed in claim 1, wherein said dynamic lens comprises a silicone or acrylic material.

11. The accommodating intraocular lens as claimed in claim 1, wherein said lens-shaping member and said first and second lens supporting members comprise polymethyl methacrylate.

12. The accommodating intraocular lens as claimed in claim 1, wherein said second lens supporting member includes a static, non-accommodating lens having an optical axis aligned with an optical axis of said dynamic lens.

13. The accommodating intraocular lens as claimed in claim 1, wherein said intraocular lens is implantable in an individual's capsular bag from which a natural lens has been removed and wherein the distal end regions of said first and second lens supporting members are configured for direct contact with said ciliary body region.

14. The accommodating intraocular lens as claimed in claim 13, wherein said flexible member and said flexible portion of the lens-shaping member each have a larger diameter condition corresponding to an expanded diameter of the dynamic lens and a smaller diameter condition corresponding to a reduced diameter of the dynamic lens, and wherein said flexible member and said flexible portions of the lens-shaping member are configured for elastically returning to said smaller diameter conditions in response to said contraction of said ciliary muscle and for elastically returning to said larger diameter conditions in response to said relaxation of said ciliary muscle.

15. The accommodating intraocular lens as claimed in claim 13, wherein said elastically flexible member is responsive to a compressive force applied to the distal end regions of said first and second lens support members by said ciliary body region upon contraction of said ciliary muscle by squeezing said flexible portions of the lens-shaping member, thereby reducing a diameter of said dynamic lens and increasing said surface curvature of said dynamic lens.

16. The accommodating intraocular lens as claimed in claim 1, wherein said intraocular lens is implantable in an anterior chamber of the eye with the distal end region of said first lens supporting member directly contacting said ciliary body region, and with said second lens supporting member attached to an iris region of said eye.

17. The accommodating intraocular lens as claimed in claim 16, wherein said flexible member and said flexible portions of the lens-shaping member each have a larger diameter condition corresponding to an expanded diameter of the dynamic lens and a smaller diameter condition corresponding to a reduced diameter of the dynamic lens, and wherein said flexible member and said flexible portions of the lens-shaping member are responsive to reduction of a compressive force applied to the distal end region of said first lens supporting member by said ciliary body region upon relaxation of said ciliary muscle by elastically returning to said larger diameter conditions, thereby elastically expanding a diameter of said dynamic lens and elastically decreasing said surface curvature of said dynamic lens to a non-accommodating condition.

18. The accommodating intraocular lens as claimed in claim 17, wherein said flexible member is responsive to a compressive force applied to said first lens supporting member by said ciliary body region upon contraction of said ciliary muscle by squeezing said flexible portions of the lens-shaping member, thereby elastically reducing the diameter of said dynamic lens, and elastically increasing said surface curvature of said dynamic lens to an accommodating condition.

19. An accommodating intraocular lens, comprising:
a lens having a deformable surface; and first and second members coupled together to transfer force from the ciliary muscle to the lens, said second member comprising a strand forming a loop having a diameter which encircles at least a central portion of the lens, said first member responsive to action of the ciliary muscle to apply a first force to said second member such that the diameter of the loop changes, said second member applying a second force which acts on the circumference of the lens in response to said first force such that both the circumference and the curvature of the lens change, wherein the first member comprises a forked member that splays in response to contractions of the ciliary muscle to reduce the compression of the second member.

* * * * *